United States Patent
Marmaropoulos et al.

(10) Patent No.: US 6,668,380 B2
(45) Date of Patent: Dec. 30, 2003

(54) SELECTIVELY DETACHABLE AND WEARABLE ELECTRODE/SENSORS

(75) Inventors: George Marmaropoulos, Yorktown Heights, NY (US); Clive Van Heerden, London (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/086,006

(22) Filed: Feb. 28, 2002

(65) Prior Publication Data

US 2003/0208830 A1 Nov. 13, 2003

(51) Int. Cl.[7] ............................................... A41B 9/00
(52) U.S. Cl. ............................................................ 2/69
(58) Field of Search .......................... 2/69, 85, 93, 159, 2/227, 243.1, 455, 912; 128/DIG. 15, 639, 644; 340/573.1, 604; 600/301, 384, 388

(56) References Cited

U.S. PATENT DOCUMENTS

| | | | | |
|---|---|---|---|---|
| 3,542,010 A | * | 11/1970 | Love | 600/384 |
| 4,191,950 A | * | 3/1980 | Levin et al. | 340/604 |
| 4,239,046 A | * | 12/1980 | Ong | 128/DIG. 15 |
| 4,583,547 A | * | 4/1986 | Granek et al. | 600/388 |
| 5,263,481 A | * | 11/1993 | Axelgaard | 600/384 |
| 5,973,602 A | * | 10/1999 | Cole et al. | 2/93 |
| 6,047,203 A | * | 4/2000 | Sackner et al. | 600/301 |
| 6,070,269 A | * | 6/2000 | Tardif et al. | 2/69 |
| 6,145,551 A | * | 11/2000 | Jayaraman et al. | 139/387 R |

* cited by examiner

Primary Examiner—Gary L. Welch
(74) Attorney, Agent, or Firm—Aaron Waxler

(57) ABSTRACT

A wearable garment for selectively retaining one or more separable and/or replaceable electrodes or sensors. The wearable garment having a flexible body with an inner surface for positioning the sensors relative to the skin of a wearer, one or more first flexible electrically conductive fasteners affixed to the inner surface, and one or more flexible electrical conductors also affixed to the inner surface so as to electrically cooperate with the one or more first flexible electrically conductive fasteners. The one or more separable and/or replaceable flexible sensors each having a second flexible electrically conductive fastener for separably fastening to the one or more first flexible electrically conductive fasteners to facilitate a complementary electrical connection between the one or more selectively separable and/or flexible sensors and the one or more flexible electrical conductors.

13 Claims, 1 Drawing Sheet

SELECTIVELY DETACHABLE AND WEARABLE ELECTRODE/SENSORS

BACKGROUND OF THE INVENTION

1. Field of the Invention

This invention relates to garments carrying electrode/sensors used in the electrical treatment and monitoring of human and animal bodies. More specifically, the invention relates to wearable garments having incorporated electrode/sensors that can be attached and detached readily for replacement and/or cleaning without undue effort and without adverse effect on the electrical connections between the sensor and the garment and related equipment such as monitoring devices and power supplies.

2. Description of the Invention

Sensing and treatment devices for contacting the surface of the skin are well-known in the art. In the previous disclosure of garments having one or more incorporated electrical sensors, there is no disclosure or suggestion that the sensor may be mounted so as to be detachable from the garment to facilitate cleaning, replacing or disposing of sensors that have been used. It will be recognized, readily, that such replacement or cleaning of previously used sensors will often be required to meet the high levels of hygiene and sterility demanded by contemporary medical standards and procedures. Similarly, there is no disclosure or suggestion in the prior art that sensors may be mounted for easy separation from, and reattachment to, a wearable garment while allowing the connectable electrical circuits for the sensors to remain in place in the garment.

These limitations of the prior art are overcome in the present invention by allowing sensors to be conveniently and detachably attached to the inner surface of a wearable garment, such as a shirt or a jacket, while the electrical circuits that are separably coupled to the sensors and that serve, in turn, to couple desired apparatus to the sensors, remains in place, with the body of the garment.

SUMMARY OF THE INVENTION

The present invention discloses a garment with sensors having a contact surface formed of flexible conductive silicone backed by, and electrically coupled to, one half of an electrically conductive separable fastener such as hook-and-loop material of the type commercially available under the Trademark VELCRO. The hook and loop material is formed of any suitable, flexible and conductive material of conventional type, that can be incorporated into the body of a wearable, washable or otherwise cleanable, garment.

A mating part of the separable fastener, for example, hook-and-loop material similarly formed of flexible conductive material, is attached to the inner surface of the garment in a desired location, and is electrically connected to durable electrical conductors incorporated into the body of the garment via printing or weaving of conductive fibers, for example. By engaging the two parts of the separable fastener, the sensor is detachably coupled to the garment as well as to the incorporated conductors, and the incorporated conductors then are capable of conducting electrical/electronic signals to and/or from the sensor surface via the fastener.

A second separable fastener arrangement at the other end of the conductor permits the conductor to be coupled detachably to external monitoring or treatment equipment of any suitable and desired type. This second fastener may be the same as or different from the separable fastener associated with the detachable electrode at the other end of the conductor. That is, one half-section of a flexible separable fastener of electrically conductive material is associated with the end of the conductor remote from the detachable electrode; it may be incorporated into the body structure of the wearable garment on either the inner or outer surface, or it may simply be attached to the remote end of the conductor free of the garment, if desired. This second fastener arrangement is completed by a mating fastener half-section of conductive material, having means to electrically couple the conductor to desired equipment when it the two half-sections are engaged with each other.

These and other and further features and advantages of the system and apparatus of this invention will be made more apparent to those having skill in this art, by reference to the following specification considered in conjunction with the accompanying drawings.

DETAILED DESCRIPTION OF THE DISCLOSED EMBODIMENT

In the following description, for purposes of explanation rather than limitation, specific details are set forth such as the particular architecture, interfaces, techniques, etc., in order to provide a thorough understanding of the present invention. However, it will be apparent to those skilled in the art that the present invention may be practiced in other embodiments, which depart from these specific details. For purposes of simplicity and clarity, detailed descriptions of well-known devices, circuits, and methods are omitted so as not to obscure the description of the present invention with unnecessary detail.

Figure 1:
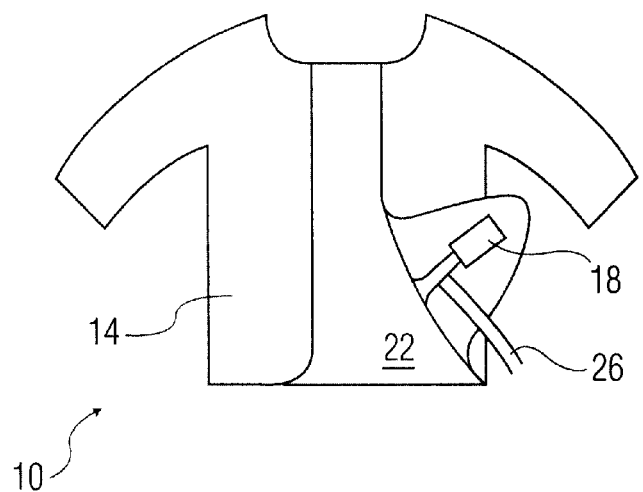
FIG. 1 is simplified pictorial representation of a wearable garment of the type used for this invention.
Figure 2:
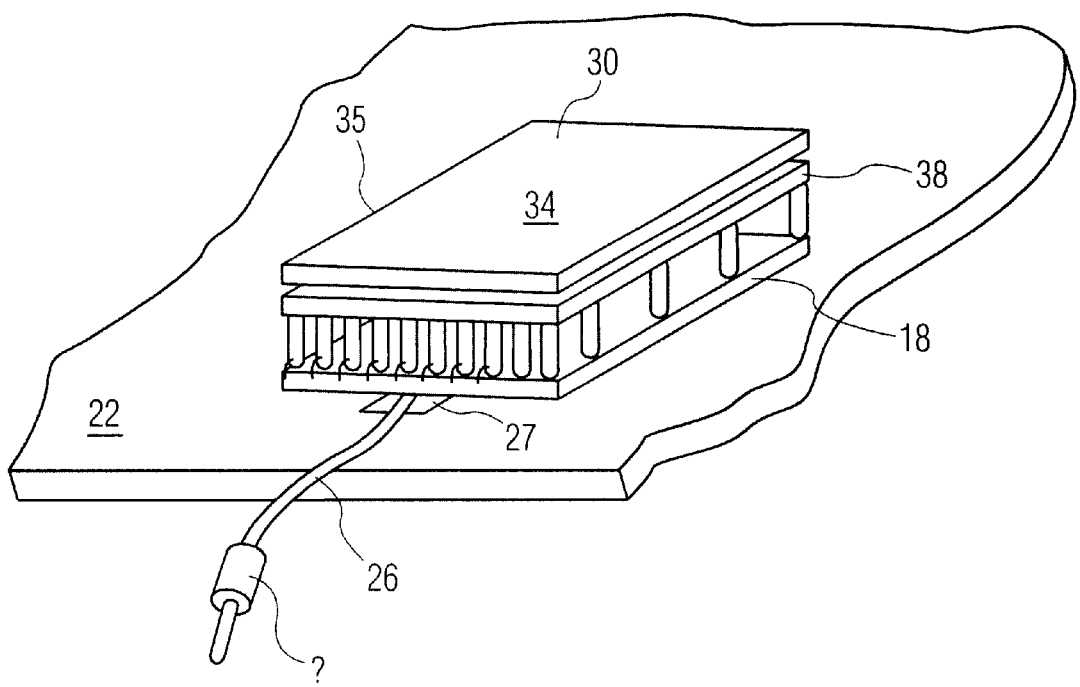
FIG. 2 is a simplified pictorial representation of a portion of the garment of FIG. 1, constructed in accordance with this invention.

Referring now to FIGS. 1 and 2 of the drawings, a wearable shirt garment 10 constructed in accordance with this invention may be seen to comprise a body structure 14 having one half of a hook and loop fastener 18, formed of a conductive fabric, secured to the inner surface 22 of garment 10. One or more flexible electrical conductors 26, electrically coupled to, and extending from, conductive hook and loop fastener 18 are mounted to the inner surface 22 of garment 10. A detachable sensor/electrode 30, having a conductive silicone contact surface 34, and a conductive hook and loop backing 38, electrically connects to conductor 26 when the mating hook-and loop fastener strips 18,38 are engaged to each other in their characteristic and well-known manner. Sensor 30 is positioned on the body of garment 10 in a predetermined location selected to place it in substantially opposed relationship with a desired surface location on the body of a wearer of the garment.

To facilitate electrical connection of conductors 26 to hook and loop strip 18, the conductors may be formed as a one-piece unit with a conductive backing element 27, and fastener 18 may then be secured in direct physical and electrical contact with backing 27. Electrical conductors 26, extending from sensor 30 may be formed and attached to the body of garment 10 in various manners within the scope of this invention. For example conductors 26 and backing 27 may be printed or otherwise deposited directly onto the fabric of the inner surface 22 of garment 10 in the form of a suitable coating material such as electrically conductive ink, paint or dye. Alternatively, conductors 26 and backing 27 may be woven or similarly integrated into the material of surface 22, as an integral part thereof, using conductive fibers, while the principal part of the material that forms surface 22 and supports conductor or conductors 26, whether it is fibrous or another form of suitable material, is electrically non-conductive. It should be understood that one or more of conductors 26 and backing 27 may be formed separately of different materials, if desired, although it is considered preferable for the two to be integrally formed. Further, if desired in view of cost or other considerations, a conductor 26 may be electrically and mechanically coupled directly to fastener 18 without use of an intermediate backing member 27.

Sensor/electrode 30 is an essential element of this invention. It comprises two significant features, namely, a flexible contact surface 34, and fastener half-section formed of flexible conductive material. In the preferred form here disclosed, contact surface 34 is formed of conductive silicone, and fastener half-section 38 comprises a hook and loop mating strip. Flexibility is a particularly desirable characteristic of contact surface 34 for use in this invention because it avoids the possibility of undesirable chafing and skin abrasion which would be likely to result from engagement of living skin tissue with the hard edge of a rigid contact/sensor structure 34 at the edge 35 where such a sensor ends and the soft inner surface 22 of supporting garment 10 begins. The silicone material of contact surface 34 must be electrically conductive to satisfy the well-known electrical operating requirements of electrode contact sensors.

Hook and loop mating strip 38 mates with, and secures itself to, a complementary mating strip 18 on inner surface 22 of garment 10, in a conventional manner. Hook and loop fastener strips and patches, as mentioned above, are well-known and are commercially available under the Trademark VELCRO. It is understood that such mating strips customarily comprise two different forms, one representing a "hook" surface, and the other representing a "loop" surface. Such fasteners may be formed as desired of any suitable form of plastic or other moldable material. For the purposes of this invention, a durable, cleanable plastic material is preferred with the added requirement that the plastic must be electrically conductive. Plastic materials meeting the requirements of durability, cleanability and electrical conductivity are well-known and widely available; to avoid confusion and prolixity, the nature and structure of these strips and these materials are not further discussed or described in this disclosure.

It will now be apparent to those having reasonable skill in this art, that a wearable garment 10 constructed in accordance with this invention will provide medical contact sensors 30 positioned on the inner surface 22 of a wearable garment in predetermined position to contact a desired location on the wearer's skin. The sensors 30 can be detached readily from garment 10 by separating electrically conductive fastener parts 18, 38 in a conventional manner. Cleaned, renewed or replacement sensors 30 can be installed with equal ease simply by rejoining the replacement, bearing a suitable fastener half-section 38, to the fastener half-section 18 that is carried on the inner surface 22 of garment 10.

While the preferred embodiments of the present invention have been illustrated and described, it will be understood by those skilled in the art that various changes and modifications may be made, and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

What is claimed is:

1. A wearable garment for positioning replaceable sensors relative to the skin of a wearer, comprising:
    a wearable body structure, of flexible material, having an inner surface;
    a flexible electrical conductor affixed to said inner surface;
    a first separable fastener, positioned relative to the skin of the wearer, affixed to said inner surface of said wearable body structure, said first separable fastener being formed of flexible electronic conductive material, and being electrically connected to said flexible electrical conductor,
    a separable unattached sensor formed of flexible conductive material having a second fastener formed of flexible conductive material electrically connected thereto, said second separable fastener being configured for separable fastening to said first separable fastener and positioned relative to the skin of the wearer to complete an electrical current path between said sensor and said electrical conductor.

2. The wearable garment of claim 1, wherein said flexible electrical conductor further has a first end electrically connected to said first separable fastener portion and a second end portion.

3. The wearable garment of claim 1, wherein said electrical conductor is integrated into the flexible material of said wearable body structure in the form of fibers of conductive material supported by fibers of substantially non-conductive material.

4. The wearable garment of claim 1, wherein said electrical conductor is printed on said inner surface of said wearable body structure in the form of electrically conductive coating material.

5. The wearable garment of claim 1, wherein said first and second separable fasteners comprise hook and loop material.

6. The wearable garment of claim 1, wherein said flexible conductive material of said sensor is conductive silicone.

7. The wearable garment of claim 1, further comprising a third separable fastener formed of electrically conductive material, electrically connecting external electrical equipment to said conductor.

8. A wearable garment for positioning replaceable sensors relative to the skin of a wearer, comprising:
    a wearable body structure, of flexible material, having an inner surface;
    a flexible electrical conductor affixed to said inner surface;
    a first separable fastener, positioned relative to the skin of the wearer affixed to said inner surface of said wearable body structure, said first separable fastener being formed of flexible electronic conductive hook and loop material, and being electrically connected to said flexible electrical conductor,
    a separable unattached sensor formed of flexible conductive silicone having a second fastener formed of flexible conductive hook and loop material electrically connected thereto, said second separable fastener being configured for separable fastening to said first separable fastener and positioned relative to the skin of the wearer to complete an electrical current path between said sensor and said electrical conductor.

9. The wearable garment of claim 8, wherein said electrical conductor is integrated into the flexible material of said wearable body structure in the form of fibers of conductive material supported by fibers of substantially non-conductive material.

10. The wearable garment of claim 8, wherein said electrical conductor is printed on said inner surface of said wearable body structure in the form of electrically conductive coating material.

11. The wearable garment of claim 8, wherein said electrical conductor further has a first end portion and a second end portion.

12. The wearable garment of claim 8, further comprising a third separable fastener formed of electrically conductive material, electrically connecting external electrical equipment to said conductor.

13. A wearable garment/sensor system, comprising;

a flexible body structure having an inner surface;

one or more first flexible electrically conductive fasteners, positioned relative to the skin of the wearer, affixed to said inner surface of said flexible body for retaining one or more selectively separable and/or replaceable flexible sensors;

one or more flexible electrical conductors, positioned relative to the skin of the wearer, affixed to said inner surface and electrically cooperating with said one or more first flexible electrically conductive fasteners;

wherein said one or more selectively unattached separable and/or replaceable flexible sensors each have a second flexible electrically conductive fastener for selectively fastening to said one or more first flexible electrically conductive fasteners to facilitate a selective complementary electrical connection between said one or more selectively separable and/or flexible sensors and said one or more flexible electrical conductors.

* * * * *